US009285508B2

(12) United States Patent  
Nunez et al.

(10) Patent No.: US 9,285,508 B2
(45) Date of Patent: Mar. 15, 2016

(54) BIOMEDICAL DEVICES

(75) Inventors: Ivan M. Nunez, Penfield, NY (US); Jay F. Kunzler, Canandaigua, NY (US); Jeffrey G. Linhardt, Fairport, NY (US); Jennifer Hunt, Batavia, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 563 days.

(21) Appl. No.: 12/456,423

(22) Filed: Jun. 16, 2009

(65) Prior Publication Data

US 2010/0318185 A1    Dec. 16, 2010

(51) Int. Cl.
| | |
|---|---|
| *C08L 83/04* | (2006.01) |
| *C08L 83/10* | (2006.01) |
| *A61L 27/18* | (2006.01) |
| *G02B 1/04* | (2006.01) |
| *A61L 27/52* | (2006.01) |
| *A61L 29/06* | (2006.01) |
| *A61L 29/14* | (2006.01) |

(52) U.S. Cl.
CPC .............. *G02B 1/043* (2013.01); *A61L 27/18* (2013.01); *A61L 27/52* (2013.01); *A61L 29/06* (2013.01); *A61L 29/145* (2013.01)

(58) Field of Classification Search
CPC .............. C09D 153/00; C08F 2438/03; C08F 293/005; C08F 83/10; A61F 2/16; A61F 2/14; G02B 1/04; G02C 7/04
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deichert et al. | |
| 4,197,266 A | 4/1980 | Clark et al. | |
| 4,327,203 A | 4/1982 | Deichert et al. | |
| 4,355,147 A | 10/1982 | Deichert et al. | |
| 4,555,732 A | 11/1985 | Tuhro | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,270,418 A | 12/1993 | Kunzler et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 2004/0138323 A1* | 7/2004 | Stenzel-Rosebaum et al. | 521/142 |
| 2006/0067981 A1* | 3/2006 | Xia | 424/428 |
| 2006/0209253 A1* | 9/2006 | Giles | 351/160 R |
| 2007/0197733 A1* | 8/2007 | Salamone et al. | 525/242 |
| 2008/0124378 A1* | 5/2008 | Byrne et al. | 424/429 |

FOREIGN PATENT DOCUMENTS

| | | |
|---|---|---|
| JP | 2008-289468 A1 | 12/2008 |
| WO | WO 96/31792 | 10/1996 |

OTHER PUBLICATIONS

Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
U.S. Appl. No. 61/113,736, filed Nov. 12, 2008, McGee.
U.S. Appl. No. 61/113,739, filed Nov. 12, 2008, McGee.
U.S. Appl. No. 61/113,742, filed Nov. 12, 2008, Nunez.
U.S. Appl. No. 61/113,746, filed Nov. 12, 2008, Nunez.
International Search Report (PCT/ISA/210) and Written Opinion (PCT/ISA/237) mailed on Sep. 28, 2010.
Pai, T S C et al. "Synthesis of Amphiphilic Block Copolymers based on poly(dimethylsiloxane) via fragmentation . . . " in J. Polymer, vol. 45, No. 13, Jun. 1, 2004, pp. 4383-4389.
Mayadunne R T A et al. "Living free radical polymerization with reversible addition-fragmentation chain . . . " in Macromolecules, vol. 36, No. 5, Mar. 11, 2003, pp. 1505-1513.
Pavlovic, D et al. "Synthesis of amphiphilic multiblock and triblock copolymers of polydimethylsiloxane . . . " in J. Polym. Sci., vol. 46, No. 21, Nov. 1, 2008, pp. 7033-7048.
Bernard, J et al. "Poly(vinyl ester) star polymers via xanthate-mediated living radical polymerization . . . " in Macromolecules, vol. 38, No. 13, Jun. 28, 2005, pp. 5475-5484.
The Office Action issued in couunterpart Japanese Patent Application No. 2012-516146 dated Jun. 10, 2014.

* cited by examiner

*Primary Examiner* — Mark Kaucher
(74) *Attorney, Agent, or Firm* — Toan P. Vo

(57) ABSTRACT

Biomedical devices such as contact lenses formed from a polymerization product of a mixture comprising (a) a multi-armed macromonomer comprising multiple side chains attached to a nucleus, wherein each side chain comprises a thio carbonyl thio fragment of the same or different reversible addition fragmentation chain transfer ("RAFT") agent; and (b) one or more biomedical device-forming monomers are disclosed.

18 Claims, No Drawings

BIOMEDICAL DEVICES

BACKGROUND OF THE INVENTION

1. Technical Field

The present invention generally relates to biomedical devices such as ophthalmic lenses.

2. Description of Related Art

Biomedical devices such as ophthalmic lenses made from siloxy-containing materials have been investigated for a number of years. Such materials can generally be sub-divided into two major classes, namely hydrogels and non-hydrogels. Hydrogels can absorb and retain water in an equilibrium state whereas non-hydrogels do not absorb appreciable amounts of water. Regardless of their water content, both hydrogel and non-hydrogel siloxy and/or fluorinated contact lenses tend to have relatively hydrophobic, non-wettable surfaces.

Hydrogels represent a desirable class of materials for many biomedical applications, including contact lenses and intraocular lenses. Hydrogels are hydrated, crosslinked polymeric systems that contain water in an equilibrium state. Silicone hydrogels are a known class of hydrogels and are characterized by the inclusion of a siloxy-containing material. Typically, a siloxy-containing monomer is copolymerized by free radical polymerization with a hydrophilic monomer, with either the siloxy-containing monomer or the hydrophilic monomer functioning as a crosslinking agent (a crosslinker being defined as a monomer having multiple polymerizable functionalities) or a separate crosslinker may be employed. An advantage of silicone hydrogels over non-silicone hydrogels is that the silicone hydrogels typically have higher oxygen permeability due to the inclusion of the siloxy-containing monomer. Because such hydrogels are based on free radical polymerization of monomers containing a crosslinking agent, these materials are thermosetting polymers.

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, good oxygen permeability is an important characteristic for certain contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

One problem associated with silicone lenses is the surfacing of silicone chains which create hydrophobic areas on the lens. This will adversely impact wettability, eye-movement and comfort to the user.

One way to alleviate this problem is by coating the surface of silicone hydrogel contact lenses with hydrophilic coatings, such as plasma coatings.

Another way to alleviate this problem is to incorporate a relatively large amount of a hydrophilic monomer such as dimethacrylamide (DMA) and/or N-vinyl-pyrrolidone in the monomer mixture. A drawback to this approach is there is potential leaching of PVP and DMA oligomers which, because of their low reactivity to relative to methacrylates, may not be covalently incorporated into the polymer network.

Accordingly, it would be desirable to provide improved biomedical devices such as contact lenses that exhibit suitable physical and chemical properties, e.g., oxygen permeability, lubriciousness and wettability, for prolonged contact with the body while also being biocompatible. It would also be desirable to provide improved biomedical devices that are easy to manufacture in a simple, cost effective manner.

SUMMARY OF THE INVENTION

In accordance with one embodiment of the present invention, a biomedical device is provided comprising a polymerization product of a mixture comprising (a) a multi-armed macromonomer comprising multiple side chains attached to a nucleus, wherein each side chain comprises a thio carbonyl thio fragment of a reversible addition fragmentation chain transfer ("RAFT") agent; and (b) one or more biomedical device-forming monomers.

In accordance with a second embodiment of the present invention, a biomedical device is provided comprising a polymerization product of a mixture comprising (a) a multi-armed macromonomer comprising multiple side chains attached to a nucleus, wherein each side chain comprises a segment comprising hydrophobic units and a terminal thio carbonyl thio fragment of a RAFT agent; and (b) one or more biomedical device-forming monomers.

The biomedical devices of the present invention are advantageously formed from at least a multi-armed macromonomer containing multiple side chains attached to a nucleus, wherein each side chain comprises a thio carbonyl thio fragment of a RAFT agent. The multi-armed macromonomers containing multiple side chains having a thio carbonyl thio fragment of a RAFT agent are well defined multi-armed macromonomers which are capable of forming biomedical devices with a hydrophilic or lubricious (or both) surface. Hydrophilic and/or lubricious surfaces of the biomedical devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer.

DETAILED DESCRIPTION OF THE PREFERRED EMBODIMENTS

The present invention is directed to biomedical devices intended for direct contact with body tissue or body fluid. As used herein, a "biomedical device" is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices, particularly contact lenses, and most particularly contact lenses made from silicone hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

The biomedical devices of the present invention are formed from a polymerization product of a mixture comprising (a) a multi-armed macromonomer comprising multiple side chains attached to a nucleus, wherein each side chain comprises a thio carbonyl thio fragment of a reversible addition fragmentation chain transfer ("RAFT") agent (or RAFT group); and (b) one or more biomedical device-forming monomers. Multi-armed macromonomers comprising multiple side chains having a thio carbonyl thio fragment of a RAFT agent attached to the nucleus are prepared via RAFT polymerization, i.e., monomers are polymerized via a RAFT mechanism to form the macromonomer, e.g., each side chain is a block copolymer in which the molecular weight of each of the blocks and the entire macromonomer are precisely controlled. Thus, RAFT polymerization is a radical polymerization technique that enables the multi-armed macromonomers to be prepared having a well defined molecular architecture and low polydispersity.

The RAFT agents suitable for use herein are based upon thio carbonyl thio chemistry which is well known to those of ordinary skill in the art. The RAFT agent can be, for example, a xanthate-containing compound, trithiocarbonate-containing compound, dithiocarbamate-containing compound or dithio ester-containing compound, wherein each compound contains a thiocarbonyl group and preferably a thiocarbonyl thio group. One class of RAFT agents that can be used herein is of the general formula:

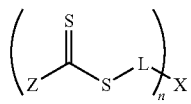

wherein Z is a substituted oxygen (e.g., xanthates (—O—R)), a substituted nitrogen (e.g., dithiocarbamates (—NRR)), a substituted sulfur (e.g., trithiocarbonates (—S—R)), a substituted or unsubstituted $C_1$-$C_{20}$ alkyl, $C_3$-$C_{25}$ unsaturated, or partially or fully saturated ring or carboxylic acid-containing group (e.g., dithioesters (—R)), n is at least 2; and R is independently a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a $C_1$-$C_{20}$ ester group; an ether or polyether-containing group; an alkyl- or arylamide group; an alkyl- or arylamine group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; and combinations thereof; L is a linking group and X comprises a nucleus. In one embodiment, n is an integer from 2 to about 10. In another embodiment, n is an integer from 3 to about 10 and preferably 3 to 6.

L is the same or different linking group and includes, by way of example, a bond, a straight or branched $C_1$-$C_{30}$ alkylene group, a $C_1$-$C_{30}$ fluoroalkylene group, a $C_1$-$C_{20}$ ester-containing group, an alkylene ether, cycloalkyl ether cycloalkenyl ether, aryl ether, arylalkyl ether, a polyether containing group, amide-containing group, amine-containing group, a substituted or unsubstituted $C_3$-$C_{30}$ cycloalkyl group, a substituted or unsubstituted $C_3$-$C_{30}$ cycloalkylalkylene group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkylene group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocyclolalkylene group, a substituted or unsubstituted $C_6$-$C_{30}$ heteroarylalkylene group, a $C_5$-$C_{30}$ fluoroaryl group, or a hydroxyl substituted alkyl ether and combinations thereof;

In one embodiment, the nucleus comprises a substituted or unsubstituted $C_1$ to $C_{30}$ alkylene group, a substituted or unsubstituted $C_5$ to $C_{30}$ cyclic or polycyclic containing group, e.g., one or more substituted or unsubstituted $C_3$-$C_{30}$ cycloalkyl group optionally containing one or more heteroatoms or one or more substituted or unsubstituted $C_6$-$C_{30}$ aryl groups optionally containing one or more heteroatoms. The cyclic group(s) can be of any molecular structure having a ring character such as at least one six membered aromatic ring, optionally having any number of such six-membered rings fused together or connected by bonds or linking structures. For example, the aromatic groups can have from 1 to about 50 such substituted or unsubstituted aromatic rings, and preferably from 1 to about 10 substituted or unsubstituted aromatic rings. If desired, when more than one cyclic containing group such as the aromatic groups are employed, the cyclic containing groups can be linked together with the same or different linking group, e.g., a $C_1$-$C_{20}$ alkylene or haloalkylene group optionally containing ether or ester linkages. Examples of an aromatic group for use herein include, but are not limited to, the following structures:

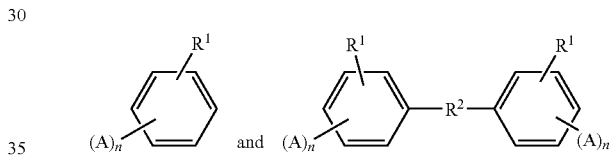

wherein A is a thio carbonyl thio group such as, for example, a group of the formula:

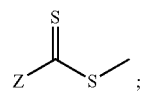

$R^1$ is independently hydrogen, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, a hydroxyl group, a $C_1$-$C_{20}$ carboxylic acid group, a $C_1$-$C_{20}$ alkoxy group, a $C_1$-$C_{20}$ ester group, an ether or polyether-containing group, an alkyl- or arylamide group, an alkyl- or arylamine group and combinations thereof, or two $R^1$ groups together with the carbon atom to which they are bonded are joined together to form a cyclic structure optionally containing one or more heterocyclic groups; $R^2$ is a bond, a $C_1$-$C_{20}$ alkylene or haloalkylene group optionally containing ether or ester linkages and Z and n have the aforestated meanings.

Representative examples of alkyl groups for use herein include, by way of example, a straight or branched alkyl chain radical containing carbon and hydrogen atoms of from 1 to about 30 carbon atoms and preferably from 1 to about 6 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of alkylene groups for use herein include, by way of example, a straight or branched alkyl chain radical containing carbon and hydrogen atoms of from 1 to about 30 carbon atoms and preferably from 1 to about 6 carbon atoms with or without unsaturation, to the rest of the molecule, e.g., methylene, ethylene, and the like.

Representative examples of cycloalkylalkyl groups for use herein include, by way of example, a substituted or unsubstituted cyclic ring-containing radical containing from about 3 to about 30 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroquinolinyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, iso-oxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocylic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined herein directly bonded to an alkyl group as defined herein. The heterocycloalkyl radical may be attached to the main structure at any carbon atom in the alkyl group that results in the creation of a stable structure.

Representative examples of hydroxyl groups for use herein include, by way of example, a hydroxy group attached directly to the rest of the molecule, i.e., —OH, or one or more hydroxy groups attached to the rest of the molecule via a linking group, e.g., an alkyl, cycloalkyl, cycloalkylalkyl, cycloalkenyl, aryl or an arylalkyl as defined herein and the like.

Representative examples of carboxylic acid-containing groups for use herein include, by way of example, a carboxylic acid group attached directly to the rest of the molecule, i.e., —COOH, or one or more carboxylic acid groups attached to the rest of the molecule via a linking group, e.g., an alkylene, cycloalkyl, cycloalkylalkylene, cycloalkenyl, aryl or an arylalkylene as defined herein and the like.

Representative examples of alkoxy groups for use herein include, by way of example, an alkyl group as defined above attached via oxygen linkage to the rest of the molecule, i.e., of the general formula —$OR^3$, wherein $R^3$ is an alkyl, cycloalkyl, cycloalkylalkyl, cycloalkenyl, aryl or an arylalkyl as defined herein, e.g., —$OCH_3$, —$OC_2H_5$, or —$O_6H_5$, and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly (alkylene oxide)s such as ethylene oxide, propylene oxide, butylene oxide, poly(ethylene oxide)s, poly(ethylene glycol) s, poly(propylene oxide)s, poly(butylene oxide)s and mixtures or copolymers thereof, an ether or polyether group of the general formula —$(R^4OR^5)_t$, wherein $R^4$ is a bond, a substituted or unsubstituted alkyl, cycloalkyl or aryl group as defined herein and $R^5$ is a substituted or unsubstituted alkyl, cycloalkyl or aryl group as defined herein and t is at least 1, e.g., —$CH_2CH_2OC_6H_5$ and $CH_2$—$CH_2$—$CH_2$—$O$—$CH_2$—$(CF_2)_z$—H where z is 1 to 6, —$CH_2CH_2OC_2H_5$, and the like.

Representative examples of alkyl or arylamide groups for use herein include, by way of example, an amide of the general formula —$R^6C(O)NR^7R^8$ wherein $R^6$, $R^7$ and $R^8$ are independently $C_1$-$C_{30}$ hydrocarbons, e.g., $R^6$ can be alkylene groups, arylene groups, cycloalkylene groups and $R^7$ and $R^8$ can be alkyl groups, aryl groups, and cycloalkyl groups as defined herein and the like.

Representative examples of alky or arylamine groups for use herein include, by way of example, an amine of the general formula —$R^9NR^{10}R^{11}$ wherein $R^9$ is a $C_2$-$C_{30}$ alkylene, arylene, or cycloalkylene and $R^{10}$ and $R^{11}$ are independently $C_1$-$C_{30}$ hydrocarbons such as, for example, alkyl groups, aryl groups, or cycloalkyl groups as defined herein.

The substituents in the 'substituted oxygen', 'substituted nitrogen', 'substituted sulfur', 'substituted alkyl', 'substituted alkylene, 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, and the like.

In another embodiment, the nucleus comprises one or more oxyalkylene units of the general formula

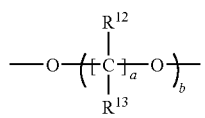

wherein $R^{12}$ and $R^{13}$ are independently hydrogen, a straight or branched $C_1$-$C_6$ alkyl group, a $C_3$-$C_{30}$ cycloalkyl group, a $C_5$-$C_{30}$ aryl group, a straight or branched $C_1$-$C_6$ fluoroalkyl group, a $C_3$-$C_{30}$ fluorocycloalkyl group, a $C_5$-$C_{30}$ fluoroaryl group, an ether group, a $C_1$-$C_{20}$ ester group, an amide group, an amine group, fluorine, a vinyl group, and a hydroxyl group, a is 1 to about 12 and preferably from 1 to about 4 and b is 1 to about 25 and preferably from 1 to about 10.

There is no particular limitation on the organic chemistry used to form the RAFT agent and is within the purview of one skilled in the art. Also, the working example below provides guidance. Representative examples of a RAFT agent include the following:

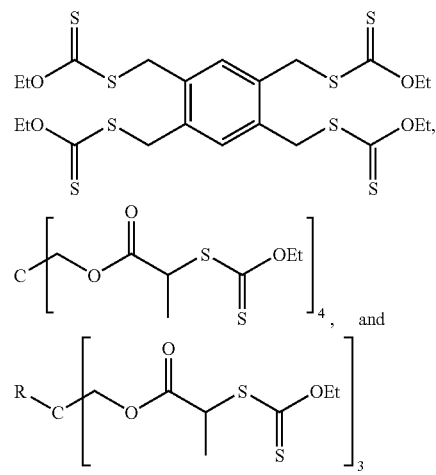

wherein R is any hydrocarbyl group.

In addition to the thio carbonyl thio fragments of a RAFT agent, the side chains of the multi-armed macromonomers described herein can also contain one or more hydrophilic units. In general, the hydrophilic unit(s) is derived from at least one ethylenically unsaturated polymerizable hydrophilic monomer. The term "ethylenically unsaturated polymerizable" as used herein shall be understood to include, by way of example, (meth)acrylate-containing radicals, (meth) acrylamide-containing radicals, vinyl-containing radicals such as vinyl radicals, vinyl carbonate-containing radicals, vinyl carbamate-containing radicals and the like, styrene-containing radicals, itaconate-containing radicals, vinyloxy-containing radicals, fumarate-containing radicals, maleimide-containing radicals, vinyl sulfonyl radicals and the like.

Suitable ethylenically unsaturated polymerizable hydrophilic monomers include, by way of example, acrylamides such as N,N-dimethylacrylamide, N,N-dimethylmethacrylamide, and the like; acetamides such as N-vinyl-N-methyl acetamide, N-vinyl acetamide and the like; formamides such as N-vinyl-N-methyl formamide, N-vinyl formamide, and the like; cyclic lactams such as N-vinyl-2-pyrrolidone and the like; (meth)acrylated alcohols such as 2-hydroxyethyl methacrylate, 2-hydroxyethyl acrylate and the like; (meth)acrylated poly(ethyleneglycol)s and the like; ethylenically unsaturated carboxylic acids such as methacrylic acid, acrylic acid and the like and mixtures thereof.

In one embodiment, the side chains of the multi-armed macromonomers can also include a unit derived from an ethylenically unsaturated polymerizable monomer having ring-opening reactive functionalities. Such monomers may include one or more ring-opening reactive groups such as, for example, azlactone, epoxy, acid anhydrides, and the like. Suitable polymerizable monomers monomer having ring-opening reactive functionalities include, but are not limited to, glycidyl methacrylate (GMA), maleic anhydride, itaconic anhydride and the like and mixtures thereof. The units derived from an ethylenically unsaturated polymerizable monomer having ring-opening reactive functionalities can be copolymerized with a hydrophilic comonomer. Non-limiting examples of comonomers useful to be copolymerized with the ring-opening reactive functionalities of the monomer to form hydrophilic units used to prepare a biomedical device include those mentioned above, preferably dimethylacrylamide, hydroxyethyl methacrylate (HEMA), and/or N-vinylpyrrolidone. Alternatively, the unit derived from the ethylenically unsaturated polymerizable hydrophilic monomers having ring-opening reactive functionalities can be subjected to a ring-opening reaction, e.g., by hydrolyzing with water, and form hydrophilic units in the resulting macromonomer.

The size of the units derived from an ethylenically unsaturated polymerizable monomer having ring-opening reactive functionalities can vary widely, e.g., the number of units can range from 0 to about 100, and preferably from about 5 to about 25.

In one embodiment, the side chains of the multi-armed macromonomers can also include a unit derived from an ethylenically unsaturated polymerizable alkoxylated polymer. Suitable ethylenically unsaturated polymerizable alkoxylated polymers include, by way of example, polymerizable polyethylene glycols having a molecular weight of up to, for example, about 1000 such as those with CTFA names PEG-200, PEG-400, PEG-600, PEG-1000, and mixtures thereof. Representative examples include PEG-200 methacrylate, PEG-400 methacrylate, PEG-600 methacrylate, PEG-1000 methacrylate and the like and mixtures thereof.

The size of the units derived from derived from an ethylenically unsaturated polymerizable alkoxylated polymer can vary widely, e.g., the number of units can range from 0 to about 750, and preferably from about 25 to about 250.

In one embodiment, the side chains of the multi-armed macromonomers can also include a unit derived from a protected monomer such as, for example, nitrogen protected monomers, acetate protected monomers, e.g., vinyl acetate, and the like. In general, nitrogen protected monomers ("NPM") have an amino group that is protected by a nitrogen protecting group. As used herein, the term "nitrogen protecting group" means a group attached to a nitrogen atom to preclude that nitrogen atom from participating in a polymerization reaction. Although secondary amine groups can be protected in accordance with the invention, in most embodiments the protected amino group provides a primary amine group following deprotection.

Suitable nitrogen protecting groups include, but are not limited to: (a) "carbamate-type" groups of the formula C(O) O—R', wherein R' is an aromatic or aliphatic hydrocarbon group, which may be optionally substituted and which, taken together with the nitrogen atom to which it is attached forms a carbamate group; (b) "amide-type" groups of the formula —C(O)—R" wherein R" is for example methyl, phenyl, trifluoromethyl, and the like, which taken together with the nitrogen atom to which they are attached form an amide group; (c) "N-sulfonyl" derivatives, that is groups of the formula —$SO_2$—R''' wherein R''' is, for example, tolyl, phenyl, trifluoromethyl, 2,2,5,7,8-pentamethylchroman-6-yl-, 2,3,6-trimethyl-4-methoxybenzene, and the like.

Representative examples of nitrogen protecting groups include, but are not limited to, benzyloxycarbonyl (CBZ), p-methoxybenzyloxycarbonyl, p-nitrobenzyloxycarbonyl, tert-butoxycarbonyl (t-BOC), 9-flourenylmethyloxycarbonyl (Fmoc), 2-chlorobenzyloxycarbonyl, allyloxycarbonyl (alloc), 2-(4-biphenylyl)propyl-2-oxycarbonyl (Bpoc), 1-adamantyloxycarbonyl, trifluoroacetyl, toluene sulphonyl and the like.

In one embodiment, examples of t-Boc protected monomers include 2-(2-(tert-butoxycarbonylamino)acetoxy)ethyl methacrylate, 2-(2-(tert-butoxycarbonylamino)acetamido) ethyl methacrylate, 2-(tert-butoxycarbonylamino)ethyl methacrylate, tert-butyl 2-(vinyloxycarbonyloxy)ethylcarbamate, 2-(tert-butoxycarbonylamino)ethyl-N-vinylcarbamate, 3-(2-(tert-butoxycarbonylamino)acetoxy)-2-hydroxypropyl, N-(tert-Butoxycarbonyl)-L-glutamic acid methacryloxyethyl ester, 2-(tert-butoxycarbonylamino)-6-(3-(2-(methacryloyloxy)ethyl)ureido)hexanoic acid, 2-(tert-butoxycarbonylamino)-3-(methacryloyloxy)propanoic acid, 2-(tert-butoxycarbonylamino)-6-methacrylamidohexanoic acid and the like.

The nitrogen protecting groups present in the side chains of the multi-armed macromonomers can be readily removed post-polymerization by well known methods in the chemical art. Techniques for protecting amino nitrogen atoms with nitrogen protecting groups, and for deprotecting amino nitrogen atoms after a particular reaction are well known in the chemical art. See, for example, Greene et al., Protective Groups in Organic Synthesis, John Wiley & Sons, 1991, and U.S. Provisional Ser. Nos. 61/113,736; 61/113,739; 61/113,742; and 61/113,746, the contents of which are incorporated by reference herein. By way of example, an NPM can be prepared by reaction of a nitrogen-protected amino acid or amino alcohol with an ethylenically unsaturated compound having a group reactive with the respective acid or an alcohol group. In some embodiments a nitrogen protected amino acid may also have an unprotected amine group or a hydroxyl group, and the second amine group or the hydroxyl group, respectively, is the site of reaction to attach the ethylenic unsaturation. If the nitrogen protected amino acid has multiple available sites of attachment of an ethylenically unsaturated group NPM monomers having two or more ethylenically unsaturated groups may be produced.

As one skilled in the art will readily understand, the protected monomers are usually hydrophobic in the "protected" or "blocked" form. In order to become more polar and hydrophilic, the protecting group (e.g., in the case of the t-Boc monomers) will need to be removed from the unit. This will result in the biomedical device becoming more hydrophilic in nature and the material could therefore retain more water. Methods for removing the protecting group are within the purview of one skilled in the art.

Generally, the size of the hydrophilic units can vary widely, e.g., the number of units can range from 1 to about 3000, preferably from about 100 to about 1000, and more preferably from about 250 to about 750.

In addition to the thio carbonyl thio fragment of a RAFT agent and optional one or more hydrophilic units, the side chains of the multi-armed macromonomers described herein may also contain one or more hydrophobic units derived from a hydrophobic ethylenically unsaturated polymerizable monomer. In one embodiment, the polymers containing one or more thio carbonyl thio fragments of a RAFT agent can include a unit derived from an ethylenically unsaturated polymerizable fluorine-containing monomer. Representative examples of a "ethylenically unsaturated polymerizable radical" include those discussed above. The ethylenically unsaturated-containing polymerizable radicals can be attached to the fluorine-containing monomer as pendent groups, terminal groups or both.

In one embodiment, useful polymerizable fluorine-containing monomers include fluorine substituted hydrocarbons having one or more polymerizable ethylenically unsaturated-containing radicals attached thereto and optionally containing one or more ether linkages, e.g., fluorine substituted straight or branched $C_1$-$C_{18}$ alkyl groups having one or more polymerizable ethylenically unsaturated-containing radicals attached thereto which may include ether linkages therebetween; fluorine substituted $C_3$-$C_{24}$ cycloalkyl groups having one or more polymerizable ethylenically unsaturated-containing radicals attached thereto which may include ether linkages therebetween; fluorine substituted $C_5$-$C_{30}$ aryl groups having one or more polymerizable ethylenically unsaturated-containing radicals attached thereto which may include ether linkages therebetween and the like.

Examples of suitable fluorine-containing monomers include, but are not limited to, 2,2,2-trifluoroethyl (meth)acrylate, 2,2,3,3-tetrafluoropropyl (meth)acrylate, 2,2,3,3,3,-pentafluoropropyl (meth)acrylate, 1-trifluoromethyl-2,2,2-trifluoroethyl (meth)acrylate, 1H,1H,5H-octafluoropentyl (meth)acrylate, octafluoropentyl vinyl carbonate, octafluoropentyl n-vinyl carbamate, hexafluoroisopropyl (meth)acrylate, 2,2,3,3,4,4-hexafluorobutyl (meth)acrylate, pentafluorophenyl (meth)acrylate, pentafluorohexyl (meth)acrylate and the like and mixtures thereof.

The size of the units derived from an ethylenically unsaturated polymerizable fluorine-containing monomer can vary widely, e.g., the number of units can range from 0 to about 400, and preferably from about 10 to about 200.

In one embodiment, the side chains of the multi-armed macromonomers containing a thio carbonyl thio fragment of a RAFT agent can also include a unit derived from an ethylenically unsaturated polymerizable ester-containing monomer. Suitable ethylenically unsaturated polymerizable ester-containing monomers include, by way of example, polymerizable fatty acid ester-containing monomers include vinyl esters made from fatty acids having from 4 to about 26 carbon atoms, and preferably from about 12 to about 16 carbon atoms in the chain. Examples of suitable fatty acid ester-containing monomers include, but are not limited to, vinyl laurate, vinyl nononoate, vinyl pivalate, vinyl crotanate, allyl crotanate, vinyl stearate and the like and mixtures thereof.

The size of the units derived from an ethylenically unsaturated polymerizable ester-containing monomer can vary widely, e.g., the number of units can range from 0 to about 400, and preferably from about 10 to about 200.

In one embodiment, the side chains of the multi-armed macromonomers containing a thio carbonyl thio fragment of a RAFT agent can also include a unit derived from an ethylenically unsaturated polymerizable polysiloxanylalkyl-containing monomer. Suitable polymerizable polysiloxanylalkyl-containing monomers include, but are not limited to, methacryloxypropyl tris(trimethylsiloxy)silane, 3-(trimethylsilyl)propyl vinyl carbonate; 3-(vinyloxycarbonylthio)propyl-[tris(trimethylsiloxy)silane]; 3-[tris(tri-methylsiloxy)silyl]propyl vinyl carbamate; 3-[tris(trimethylsiloxy)silyl] propyl allyl carbamate; 3-[tris(trimethylsiloxy)silyl]propyl vinyl carbonate, tris(trimethylsiloxy)silylpropyl methacrylamide and the like and mixtures thereof. In one embodiment, the polymerizable polysiloxanylalkyl-containing monomer is M 1-MCR—C12 as shown in the formula below:

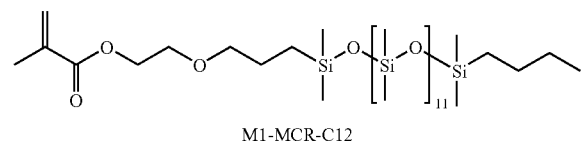

M1-MCR-C12

The size of the units derived from an ethylenically unsaturated polymerizable polysiloxanylalkyl-containing monomer can vary widely, e.g., the number of units can range from 0 to about 100, and preferably from about 5 to about 25.

Methods for preparing the multi-armed macromonomers as described above are within the purview of one skilled in the art. Also, the working examples below provide ample guidance.

The resulting multi-armed macromonomers will have a number average molecular weight ranging from about 1,000 to about 300,000 and about 10,000 to about 100,000.

The one or more comonomers employed in the mixtures to be polymerized to form a biomedical device include conventional biomedical device-forming or ophthalmic lens-forming monomers. As used herein, the term "monomer" or "monomeric" and like terms denote relatively low molecular weight compounds that are polymerizable by free radical polymerization, as well as higher molecular weight compounds also referred to as "prepolymers", "macromonomers", and related terms. Generally, the biomedical device-forming comonomer contains at least one polymerizable group. In one embodiment, a suitable comonomer includes hydrophobic monomers, hydrophilic monomers and the like and mixtures thereof.

Representative examples of hydrophilic comonomers include, but are not limited to, unsaturated carboxylic acids, such as methacrylic and acrylic acids; (meth)acrylic substituted alcohols or polyols such as 2-hydroxyethyl methacrylate, 2-hydroxyethyl acrylate, glyceryl methacrylate and the like; vinyl lactams such as N-vinylpyrrolidone and the like; and (meth)acrylamides such as methacrylamide, N,N-dimethylacrylamide and the like and combinations thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the mixtures in an amount ranging from 0 to about 70 weight percent, based on the total weight of the mixture.

According to various preferred embodiments, the initial mixture can comprise at least one (meth)acrylic substituted alcohol, such as at least one of 2-hydroxyethyl methacrylate and glyceryl methacrylate, preferably in an amount of at least about 1 weight percent of the mixture, and preferably in an amount of about 2 to about 40 weight percent. Preferably, the mixture further includes at least one vinyl lactam, such as N-vinylpyrrolidone and/or at least one (meth)acrylamide, such as N,N-dimethylacrylamide.

Suitable hydrophobic monomers include $C_1$-$C_{20}$ alkyl and $C_3$-$C_{20}$ cycloalkyl (meth)acrylates, substituted and unsubstituted $C_6$-$C_{30}$ aryl (meth)acrylates, (meth)acrylonitriles, fluorinated alkyl methacrylates, long-chain acrylamides such as octyl acrylamide, and the like. The hydrophobic monomers can be present in the mixtures in an amount ranging from 0 to about 30 weight percent, based on the total weight of the mixture.

Another class of device-forming or lens-forming monomers is silicone-containing monomers. In other words, another silicone-containing comonomer which contains from 1 to about 60 silicone atoms, in addition to the polymer containing one or more thio carbonyl thio fragments of a RAFT agent, may be included in the initial mixture, for example, if it is desired to obtain a copolymer with high oxygen permeability. Applicable silicone-containing monomers for use in the formation of contact lenses such as silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth)acrylic monomer is represented by the structure of Formula I:

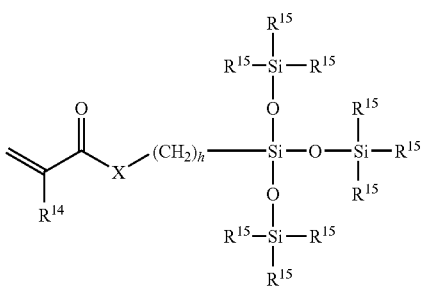

(I)

wherein X denotes —O— or —NR— wherein R denotes hydrogen or a $C_1$-$C_4$ alkyl; each $R^{14}$ independently denotes hydrogen or methyl; each $R^{15}$ independently denotes a lower alkyl radical, phenyl radical or a group represented by

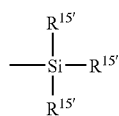

wherein each $R^{15'}$ independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Ia:

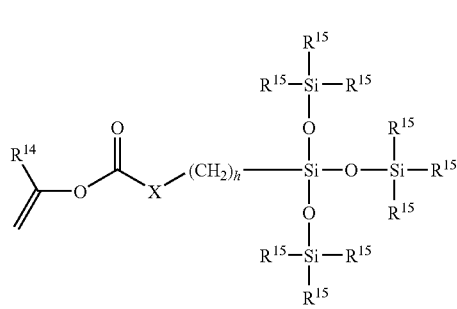

(Ia)

wherein X denotes —NR—; wherein R denotes hydrogen or a $C_1$-$C_4$ alkyl; $R^{14}$ denotes hydrogen or methyl; each $R^{15}$ independently denotes a lower alkyl radical, phenyl radical or a group represented by

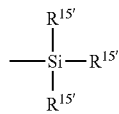

wherein each $R^{15'}$ independently denotes a lower alkyl or phenyl radical; and h is 1 to 10, and the like.

Examples of bulky monomers are 3-methacryloyloxypropyltris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]itetramethyldisiloxane; 3-(trimethylsilyl)propyl vinyl carbonate; 3-(vinyloxycarbonylthio)propyl-[tris(trimethylsiloxy)silane]; 3-[tris (trimethylsiloxy)silyl]propyl vinyl carbamate; 3-[tris (trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacrylates in Polyurethane-Polysiloxane Hydrogels," Journal of Applied Polymer Science, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula IV:

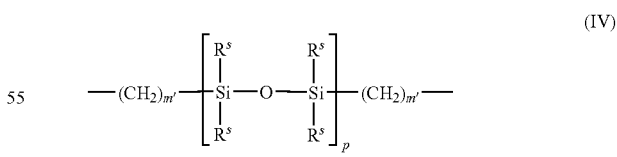

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

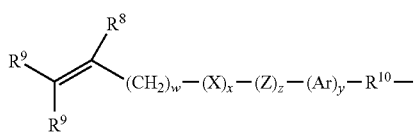

(V)

wherein: $R^8$ is hydrogen or methyl;
$R^9$ is independently hydrogen, an alkyl radical having 1 to 6 carbon atoms, or a —CO—Y—$R^{11}$ radical wherein Y is —O—, —S— or —NH—;
$R^{10}$ is a divalent alkylene radical having 1 to about 10 carbon atoms;
$R^{11}$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

A preferred silicone-containing urethane monomer is represented by Formula VI:

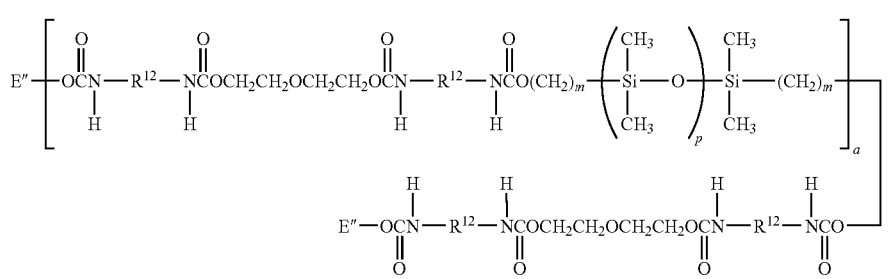

(VI)

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E" is a group represented by:

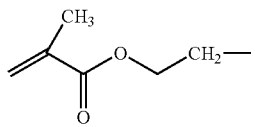

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954, 587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other biomedical devices can also be used.

For example, a biomedical device-forming comonomer can be a cationic monomer such as cationic silicone-containing monomer or cationic fluorinated silicone-containing monomers.

The mixtures may include the silicone comonomer, in addition to the subject multi-armed macromonomers, at 0 to about 50 weight percent, preferably about 5 to about 30 weight percent when present.

The mixture can also include a crosslinking monomer (a crosslinking monomer being defined as a monomer having multiple polymerizable functionalities). Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a crosslinking agent is employed, this monomeric material may be included in the monomer mixture at about 0.1 to about 20 weight percent, and more preferably at about 0.2 to about 10 weight percent.

Although not necessarily required, homopolymers or copolymers within the scope of the present invention may optionally have one or more strengthening agents added prior to polymerization, preferably in quantities of less than about 80 weight percent and preferably from about 20 to about 60 weight percent. Non-limiting examples of suitable strengthening agents are described in U.S. Pat. Nos. 4,327,203; 4,355, 147; and 5,270,418; each of which is incorporated herein in its entirety by reference. Specific examples, not intended to be limiting, of such strengthening agents include cycloalkyl acrylates and methacrylates; e.g., tert-butylcyclohexyl methacrylate and isopropylcyclopentyl acrylate.

The mixture may further contain, as necessary and within limits not to impair the purpose and effect of the present invention, various additives such as an antioxidant, coloring agent, ultraviolet absorber, lubricant internal wetting agents, toughening agents and the like and other constituents as is well known in the art.

The biomedical devices of the present invention, e.g., contact lenses or intraocular lenses, can be prepared by polymerizing the foregoing mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the biomedical devices such as contact lenses may be cast directly in molds, e.g., polypropylene molds, from the mixtures, e.g., by spincasting and static casting methods. Spincasting methods are disclosed in U.S. Pat. Nos.

3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the mixture between two mold sections, one mold section shaped to form the anterior lens surface and the other mold section shaped to form the posterior lens surface, and curing the mixture while retained in the mold assembly to form a lens, for example, by free radical polymerization of the mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 4 carbon atoms such as methanol, ethanol or propan-2-ol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. Generally, the mixture will contain the multi-armed macromonomer in an amount ranging from about 0.1 to about 15 weight percent, and preferably about 1 to about 10 weight percent, based on the total weight of the monomer mixture. The biomedical device-forming comonomer may be present in the mixture in an amount ranging from about 50 to about 99.9 weight percent, and preferably from about 75 to about 99 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the monomer mixtures may further include a monomer for increasing the refractive index of the resultant copolymer. Examples of such monomers are aromatic (meth)acrylates, such as phenyl (meth)acrylate, 2-phenylethyl (meth)acrylate, 2-phenoxyethyl methacrylate, and benzyl (meth)acrylate.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

In the examples, the following abbreviations are used.
DMA: N,N-dimethylacrylamide
HEMA: 2-hydroxyethyl methacrylate
NVP: N-vinyl-2-pyrrolidone
AIBN: azo bis-isobutylnitrile (Vazo™ 64)
TRIS: 3-methacryloxypropyltris(trimethylsiloxy)silane
HEMAVC: methacryloxyethyl vinyl carbonate
IMVT: 1,4-bis(4-(2-methacryloxyethyl)phenylamino)anthraquinone Example 1

Preparation of 1,3,4,5 Tetrakis-(ethyl xanthyl)benzene having the following structure:

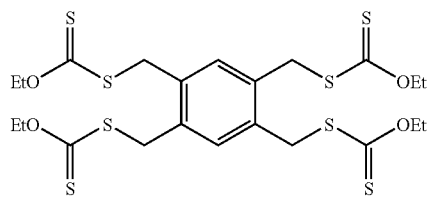 [SMILES: CCOC(=S)SCc1cc(CSC(=S)OCC)c(CSC(=S)OCC)cc1CSC(=S)OCC]

Into a 1000 mL round bottom 3 neck flask fitted with a magnetic stirrer, nitrogen inlet, Freidrich's condenser, and a temperature probe was added 2.5 g of 1,2,4,5-tetrakis (bromomethyl)benzene, 4.5 g of potassium o-ethyl xanthate, and 400 mL of 50:50 tetrahydrofuran:ethanol. The reaction flask was placed in an ice bath at 0° C. and stirred for 24 hours. Next, 250 mL of deionized water was added to the flask. The crude mixture was extracted 4 times with 250 mL of 1:1:2 methylene chloride:ethyl ether: heptane retaining the organic layers. The combined organic layers were dried over anhydrous magnesium sulfate, filtered, and solvent was removed under reduced pressure to provide the product.

Example 2

Preparation of a Multi-Armed Macromonomer having the structure:

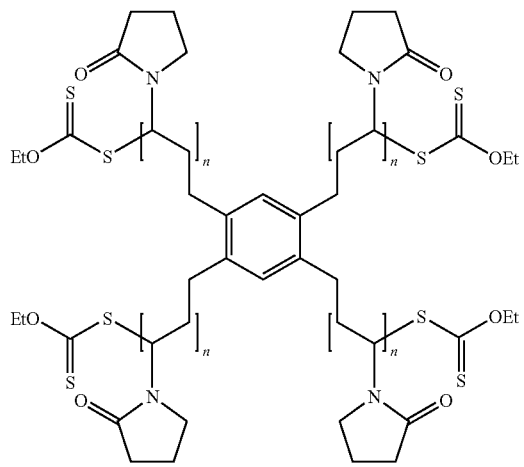

wherein each n is on average 13.

Into a one neck, 125 mL round bottom flask equipped with a magnetic stirring bar were added 480 mg of 1,2,4,5-tetrakis (ethyl xanthyl)benzene of Example 1 (0.000781 moles), 40 mL of NVP (41.6 g, 0.3743 moles), and 50 mL of anhydrous 1,4-dioxane. After these components were thoroughly mixed, 0.00517 g of AIBN (0.00000956 moles) was added to the round bottom flask. The round bottom flask was closed with an appropriately sized rubber septum and the contents of the flask were then purged by bubbling dry nitrogen gas for 1 hour at 10-15 mL/min. The contents of the reaction flask were heated to 60° C. with an oil bath (pre-set and pre-heated to ensure accurate heating) while maintaining a slow nitrogen flow (10-15 mL/min). The reaction was allowed to proceed for 18 hours under nitrogen while continuing to heat at 60° C. The reaction was then removed from the heating bath and allowed to cool to room temperature. The contents of the reaction flask were then added dropwise into 2500 mL of ether while stirring vigorously to minimize clumping of the precipitating polymer. The resulting product was then filtered and dried under vacuum to remove residual ether.

Example 3

Preparation of a Multi-Armed Macromonomer having the structure:

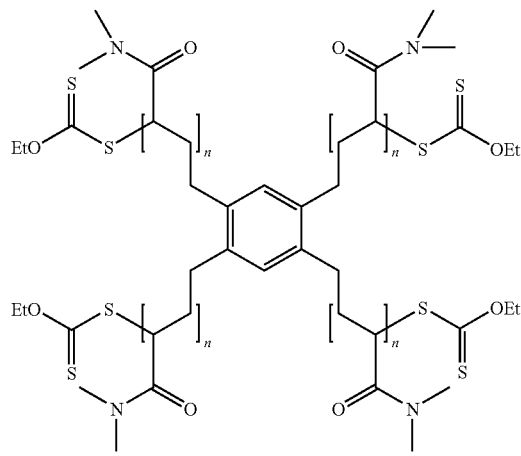

wherein each n is on average 13.

In a one neck, 125 mL round bottom flask equipped with a magnetic stirring bar were added 472 mg of 1,2,4,5-tetrakis (ethyl xanthyl)benzene of Example 1 (0.000764 moles), 40 mL of DMA (38.38 g, 0.3882 moles), and 50 mL of anhydrous 1,4-dioxane. After these components were thoroughly mixed, 0.0553 g of AIBN (0.000764 moles) were added to the round bottom flask. The round bottom flask was closed with an appropriately sized rubber septum and the contents of the flask were then purged by bubbling dry nitrogen gas for 1 hour at 10-15 mL/min. The contents of the reaction flask were heated to 60° C. with an oil bath (pre-set and pre-heated to ensure accurate heating) while maintaining a slow nitrogen flow (10-15 mL/min). The reaction was allowed to proceed for 18 hours under nitrogen while continuing to heat at 60° C. The reaction was then removed from the heating bath and allowed to cool to room temperature. The contents of the reaction flask were then added dropwise into 2500 mL of ether while stirring vigorously to minimize clumping of the precipitating polymer. The polymer product was then filtered and dried under vacuum to remove residual ether.

Example 4

Preparation of a contact lens.

A mixture is made by mixing the following components listed in Table 1, at amounts per weight percent.

TABLE 1

| Ingredient | Weight Percent |
|---|---|
| Polyurethane-siloxane prepolymer | 53 |
| TRIS | 15 |
| NVP | 33 |
| HEMA | 5 |
| HEMAVC | 1 |
| Macromonomer of Example 2 | 1 |
| N-hexanol | 15 |
| Vazo-64 | 0.5 |
| IMVT | 150 ppm |

The resulting mixture is cast into contact lenses by introducing the mixture to a mold assembly composed of an ethyl vinyl alcohol mold for the anterior surface and an ethyl vinyl alcohol mold for the posterior surface and thermally curing the mixture at 100° C. for 2 hours. The resulting contact lens is released from the mold, extracted with isopropyl alcohol for 4 hours and placed in buffer solution.

Example 5

Preparation of a contact lens.

A mixture is made by mixing the following components listed in Table 2, at amounts per weight percent.

TABLE 2

| Ingredient | Weight Percent |
|---|---|
| Polyurethane-siloxane prepolymer | 53 |
| TRIS | 15 |
| NVP | 33 |
| HEMA | 5 |
| HEMAVC | 1 |
| Macromonomer of Example 3 | 1 |
| N-hexanol | 15 |
| Vazo-64 | 0.5 |
| IMVT | 150 ppm |

The resulting mixture is cast into contact lenses by introducing the mixture to a mold assembly composed of an ethyl vinyl alcohol mold for the anterior surface and an ethyl vinyl alcohol mold for the posterior surface and thermally curing the mixture at 100° C. for 2 hours. The resulting contact lens is released from the mold, extracted with isopropyl alcohol for 4 hours and placed in buffer solution.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device comprising an in-mold polymerization product of a mixture comprising (a) a multi-armed macromonomer block copolymer comprising multiple side chains attached to a nucleus, wherein each side chain is a block copolymer comprising a thio carbonyl thio fragment of the same or different reversible addition fragmentation chain transfer (RAFT) agent, and one or more hydrophilic units, and further wherein each side chain does not contain one or more hydrophobic units; and (b) one or more biomedical device-forming monomers, wherein the biomedical device is a contact lens, an intraocular lens or a conical implant.

2. The biomedical device of claim 1, wherein the thio carbonyl thio fragment of each side chain is the same thio carbonyl thio fragment.

3. The biomedical device of claim 1, wherein the thio carbonyl thio fragment of each side chain comprises a dithioester group, xanthate group, dithiocarbamate group or trithiocarbonate group.

4. The biomedical device of claim 1, wherein the multi-armed macromonomer comprises 3 or more side chains.

5. The biomedical device of claim 1, wherein the multi-armed macromonomer comprises 3 to 1.0 side chains.

6. The biomedical device of claim 1, wherein the hydrophilic units are derived from a hydrophilic monomer selected from the group consisting of an unsaturated carboxylic acid, acrylamide, vinyl lactam, poly(alkyleneoxy)(meth)acrylate, (meth)acrylic acid, hydroxy-containing-(meth)acrylate, hydrophilic vinyl carbonate, hydrophilic vinyl carbamate monomer, hydrophilic oxazolone monomer, and mixtures thereof.

7. The biomedical device of claim 1, wherein the hydrophilic units are derived from a hydrophilic monomer selected from the group consisting of methacrylic acid, acrylic acid, 2-hydroxyethylmethacrylate, 2-hydroxyethylacrylate, N-vinyl pyrrolidone, methacrylamide, N,N-dimethylacrylamide, ethylene glycol dimethacrylate and mixtures thereof.

8. The biomedical device of claim 1, wherein the hydrophilic units are derived from an ethylenically unsaturated polymerizable alkoxylated polymer selected from the group consisting of polyethylene glycol (PEG)-200 methacrylate, PEG-400 methacrylate, PEG-600 methacrylate, PEG 1000 methacrylate and mixtures thereof.

9. The biomedical device of claim 1, wherein the hydrophilic units comprise about 100 to about 1000 units.

10. The biomedical device of claim 1, wherein the nucleus comprises a substituted or unsubstituted cyclic or polycyclic containing group.

11. The biomedical device of claim 1, wherein the nucleus comprises one or more oxyalkylene units or an alkylene group.

12. The biomedical device of claim 1, wherein the one or more biomedical device-forming monomers is a silicone-containing monomer.

13. The biomedical device of claim 1, wherein the one or more biomedical device-forming monomers is a hydrophilic monomer or hydrophobic monomer.

14. The biomedical device of claim 1, wherein the mixture further comprises a hydrophilic monomer, hydrophobic monomer or both.

15. The biomedical device of claim 1, wherein the contact lens is a rigid gas permeable contact lens.

16. The biomedical device of claim 1 wherein the contact lens is a soft contact lens.

17. The biomedical device of claim 1 wherein the contact lens is a hydrogel contact lens.

18. A biomedical device obtained by casting a mixture comprising (a) a multi-armed macromonomer block copolymer comprising multiple side chains attached to a nucleus, wherein each side chain is a block copolymer comprising a thio carbonyl thio fragment of the same or different reversible addition fragmentation chain transfer (RAFT) agent, and one or more hydrophilic units, and further wherein each side chain does not contain one or more hydrophobic units; and (b) one or more biomedical device-forming monomers, into a biomedical device by mold polymerization, wherein the biomedical device is a contact lens, an intraocular lens or a corneal implant.

* * * * *